(12) United States Patent
Bang et al.

(10) Patent No.: US 6,447,455 B2
(45) Date of Patent: Sep. 10, 2002

(54) ULTRASOUND DIAGNOSTIC APPARATUS AND METHOD FOR MEASURING BLOOD FLOW VELOCITY USING DOPPLER EFFECT

(75) Inventors: Ji Hoon Bang, Gyeonggi-do; Cheol An Kim, Seoul, both of (KR)

(73) Assignee: Medison Co., Ltd., Kangwon-Do (KR)

( * ) Notice: Subject to any disclaimer, the term of this patent is extended or adjusted under 35 U.S.C. 154(b) by 0 days.

(21) Appl. No.: 09/898,783

(22) Filed: Jul. 3, 2001

(30) Foreign Application Priority Data

Jul. 8, 2000 (KR) ........................................ 2000-39086

(51) Int. Cl.[7] ................................................ A61B 5/00
(52) U.S. Cl. ..................................................... 600/454
(58) Field of Search ................................ 600/454, 455, 600/456, 443, 447, 449, 448; 128/916

(56) References Cited

U.S. PATENT DOCUMENTS 5,676,148 A * 10/1997 Koo et al. .................. 600/443
5,895,358 A * 4/1999 Becker et al. .............. 128/916
6,210,332 B1 * 4/2001 Chiao et al. ................ 128/916
6,364,838 B1 * 4/2002 Freiburger et al. ......... 600/455

* cited by examiner

Primary Examiner—Francis J. Jaworski
Assistant Examiner—Maulin Patel
(74) Attorney, Agent, or Firm—Wiggin & Dana LLP

(57) ABSTRACT

An ultrasound diagnostic system and a method for the same update a pulse repetition frequency(PRF) by sensing an aliasing of a sampled data. A sample data generator generates sample data by transmitting an ultrasound signal into a human body and sampling a reflected signal of the ultrasound signal. A frequency distribution data generator generates a frequency distribution data by processing the sample data. A blood flow velocity detector determines a blood flow velocity on the basis of the frequency distribution data. An aliasing detector detects whether or not an aliasing occurs in the frequency distribution data. The aliasing detector computes a peak index corresponding to the fastest blood flow velocity component among the frequency components comprising the frequency distribution data, selects a frequency range having the largest sum of power levels of the frequency components between a positive frequency range and a negative frequency range, compares the selected frequency range with the peak index, and determines whether an aliasing occurs or not.

8 Claims, 7 Drawing Sheets

ULTRASOUND DIAGNOSTIC APPARATUS AND METHOD FOR MEASURING BLOOD FLOW VELOCITY USING DOPPLER EFFECT

FIELD OF THE INVENTION

The present invention relates to an ultrasound diagnostic apparatus and method for measuring a blood flow velocity using Doppler effect. More particularly, the invention relates to an ultrasound diagnostic apparatus and method that update a pulse repetition frequency(PRF) so as to prevent an aliasing in measuring a blood flow velocity using Doppler effect.

BACKGROUND OF THE INVENTION

An ultrasound diagnostic apparatus using the Doppler effect is widely used in measuring the velocity of blood flow in the human body. In such a system, an ultrasound transducer array transmits an ultrasound signal toward a moving object, e.g., red blood cells, and receives a reflected signal from the object. The apparatus computes the frequency shift or phase shift of the reflected signal with respect to the transmitted signal in order to determine the velocity of the moving object.

FIG. 1 is a block diagram of a conventional ultrasound diagnostic apparatus 10 for measuring the velocity of blood flow in a human body. The apparatus 10 comprises a transducer array 103, a pre-amplifier 104, a time-variable gain compensator (TGC) amplifier 105, an analog-to-digital (A/D) converter 106, a quadrature demodulator 107, a digital signal processor 108, a display device 109, and a peak blood flow velocity detector 110.

Specifically, the transducer array 103 first transmits an ultrasound signal to an object (not shown), e.g., red blood cells in a human body, and receives a reflected signal from the object possibly with noise. The received signal is then applied to the pre-amplifier 104 for pre-amplification. The output of the pre-amplifier 104 is amplified at the TGC amplifier 105 with a time-varying gain in order to compensate attenuation due to propagation distance of the ultrasound signal in the human body. The output of the TGC amplifier 105 is converted to a digital signal at the analog-to-digital (A/D) converter 106. The digital signal is demodulated at a quadrature demodulator 107. The demodulated signal is applied to the digital signal processor 108 where the velocity of the object is computed. The velocity is displayed at the display device 109 for human users.

In the digital signal processor 108, the demodulated signal undergoes clutter filtering, fast Fourier transforming (FFT) and post-processing to obtain the velocity distribution spectrum. That is, the clutter that is reflected from slowly moving organ and muscle compared to the blood is removed from the demodulated signal by a high-pass filter (not shown). Then, in the digital signal processor 108, frequency distribution data of 2N frequency components is generated from the filtered signal by using a well known FFT technique. Finally, as post-processing, a known signal processing such as the log compression and base line shifting is performed on the frequency distribution data corresponding to the velocity distribution spectrum.

In order to measure a blood flow velocity of the human body by using the Doppler effect, it is desirable to measure the mean velocity and the peak velocity of the blood flow because blood flow is actually a collection of many blood cells that do not move uniformly in one direction. In other words, at one instant of time, blood cells exhibit different velocities and moving directions. As a result, when an ultrasound signal of a given frequency is transmitted to these cells, its reflected ultrasound signal from the cells would be composed of many different frequencies around the given frequency because these different velocities would bring about different Doppler frequency shifts. Further, the reflected ultrasound signal inevitably includes noise in addition to an ideally reflected signal from the object. The noise, of course, should be isolated from the reflected signal components to accurately determine the mean and peak velocities of the blood flow. Typically, to isolate the noise from the reflected signal, a noise threshold is established so that frequency components of the reflected signal whose power levels are below the noise threshold could be discarded as noise.

FIG. 2 is a frequency distribution of the reflected ultrasound signal from a target blood flow. Note that the center frequency has been shifted to zero in order to graphically illustrate the directions of blood cells. Frequency components in the negative domain represent frequency shifts of the ultrasound signal that reflected off blood cells that move away from the transducer shown in FIG. 1. Conversely, those in the positive domain represent frequency shifts of the ultrasound that reflected off those blood cells that move toward the transducer. It is well known in the art that, if a frequency shift is detected, then the velocity of a moving object that caused the shift can be computed as they are proportional to each other. In the graph of FIG. 2, a velocity corresponding to $f_p$ is considered as the peak velocity because it is farthest from the center frequency (thus being greatest frequency shift) and its power is above the noise threshold 203. The peak velocity is detected at the peak blood flow velocity detector 110 shown in FIG. 1. And, the mean velocity is obtained by computing the mean of all the velocities corresponding to the frequency components whose power levels are above the noise threshold.

As described above, it is important to accurately determine the noise threshold, i.e., the power level that discriminates between the noise and the purely reflected signal, in the computation of the mean and peak velocities of the blood flow. One of known methods for determining a noise threshold is to use the mean power of frequency components in a selected frequency range far higher than the transmitted frequency, i.e., in a frequency range where no reflected frequency components are expected. For example, the mean of power levels of highest frequencies from the frequency distribution of a received signal was used as the noise threshold. The hypothesis behind this conventional method is that random noise tends to have a flat power spectrum so that the power levels of frequencies where desired signals are not present would be that of the noise.

However, the conventional method failed take into consideration whether those frequency components used to determine the noise threshold are in the positive frequency domain or negative frequency domain. Furthermore, it was based on the hypothesis that no purely-reflected signal would exist in the far end ranges of the frequency distribution. However, such an assumption is useful only if a PRF (pulse repetition frequency) is sufficiently higher than the blood flow velocity. If not, aliasing occurs. That is, some of the highest negative frequency components appear in the positive frequency domain and vice versa. The aliasing will result in the setting of a noise threshold that is actually not just the power of noise but includes some signal components.

SUMMARY OF THE INVENTION

It is, therefore, an objective of the present invention to provide an ultrasound diagnostic apparatus and method that determine whether or not an aliasing occurs in sample data in measuring a blood flow velocity of human body.

It is another objective of the present invention to provide an ultrasound diagnostic apparatus and method for updating a pulse repetition frequency (PRF) so as to prevent an aliasing of sample data in measuring blood flow velocity of human body.

In order to achieve these objectives, an ultrasound diagnostic apparatus for measuring a blood flow velocity using the Doppler effect includes: means for generating sample data by transmitting an ultrasound signal into a human body and sampling a reflected signal of the ultrasound signal; means for generating frequency distribution data by processing the sample data, wherein the frequency distribution data includes a number of frequency components, each of the frequency components having a corresponding power level; means for detecting a blood flow velocity on the basis of the frequency distribution data; and means for detecting whether or not an aliasing occurs in the frequency distribution data, wherein the means for detecting the aliasing computes a peak index corresponding to the fastest blood flow velocity component among the frequency components comprising the frequency distribution data, selects a frequency range having the largest sum of power levels of the frequency components between a positive frequency range and a negative frequency range, compares the selected frequency range with the peak index, and determines whether an aliasing occurs or not.

The ultrasound diagnostic apparatus further includes means for updating a pulse repetition frequency(PRE) generating the sample data when the means for detecting the aliasing detects the aliasing of sample data, in order to prevent the aliasing.

An ultrasound diagnostic method for measuring a blood flow velocity includes the steps of: (a) generating sample data by transmitting an ultrasound signal into a human body and sampling a reflected signal of the ultrasound signal; (b) generating frequency distribution data by processing the sample data, wherein the frequency distribution data includes a number of frequency components, each of the frequency components having a corresponding power level; (c) detecting a blood flow velocity on the basis of the frequency distribution data; and (d) determining whether or not an aliasing occurs in the frequency distribution data, wherein the step for determining the aliasing computes a peak index corresponding to the fastest blood flow velocity component among the frequency components comprising the frequency distribution data, selects a frequency range having the largest sum of power levels of the frequency components between a positive frequency range and a negative frequency range, compares the selected frequency range with the peak index, and determines whether an aliasing occurs or not.

The ultrasound diagnostic method further includes the step (e) for updating a pulse repetition frequency(PRF) of the sample data if the aliasing occurs.

BRIEF DESCRIPTIONS OF THE DRAWINGS

The above and other objects and features of the present invention will become apparent from the following description of preferred embodiments given in conjunction with the accompanying drawings, in which.

DETAILED DESCRIPTION OF THE PRESENT INVENTION

An embodiment of the present invention will now be described in detail in reference to the accompanying drawings.

Figure 1:
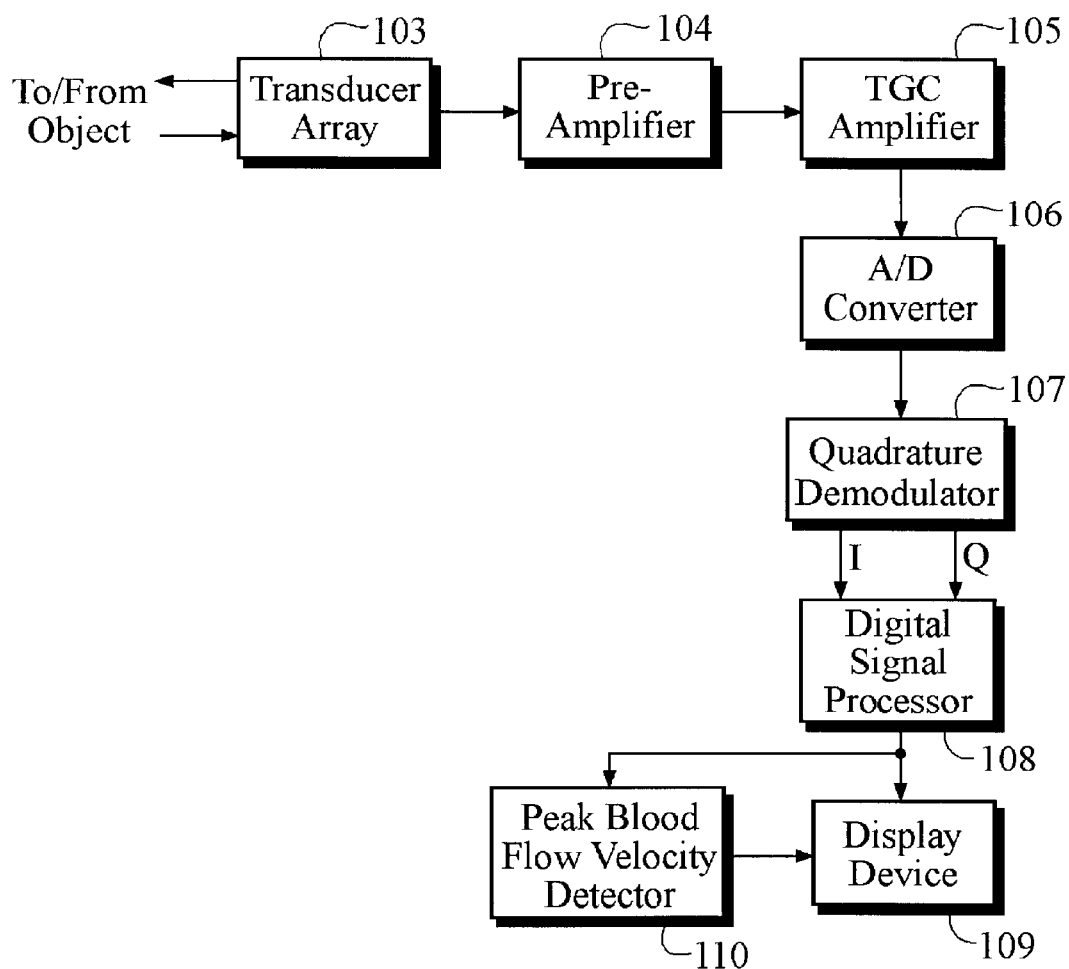
FIG. 1 is a block diagram of a conventional ultrasound diagnostic apparatus for measuring blood flow velocities.
Figure 2:
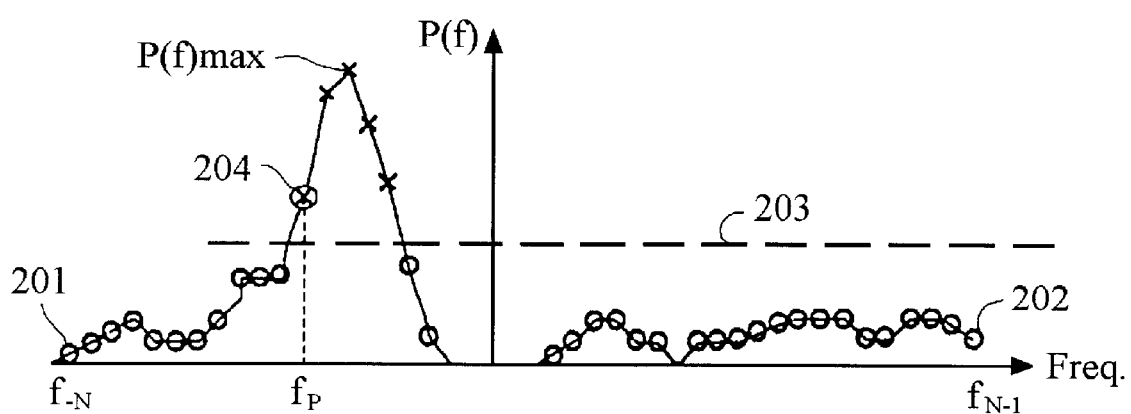
FIG. 2 illustrates the frequency distribution of a reflected ultrasound signal.
Figure 3:
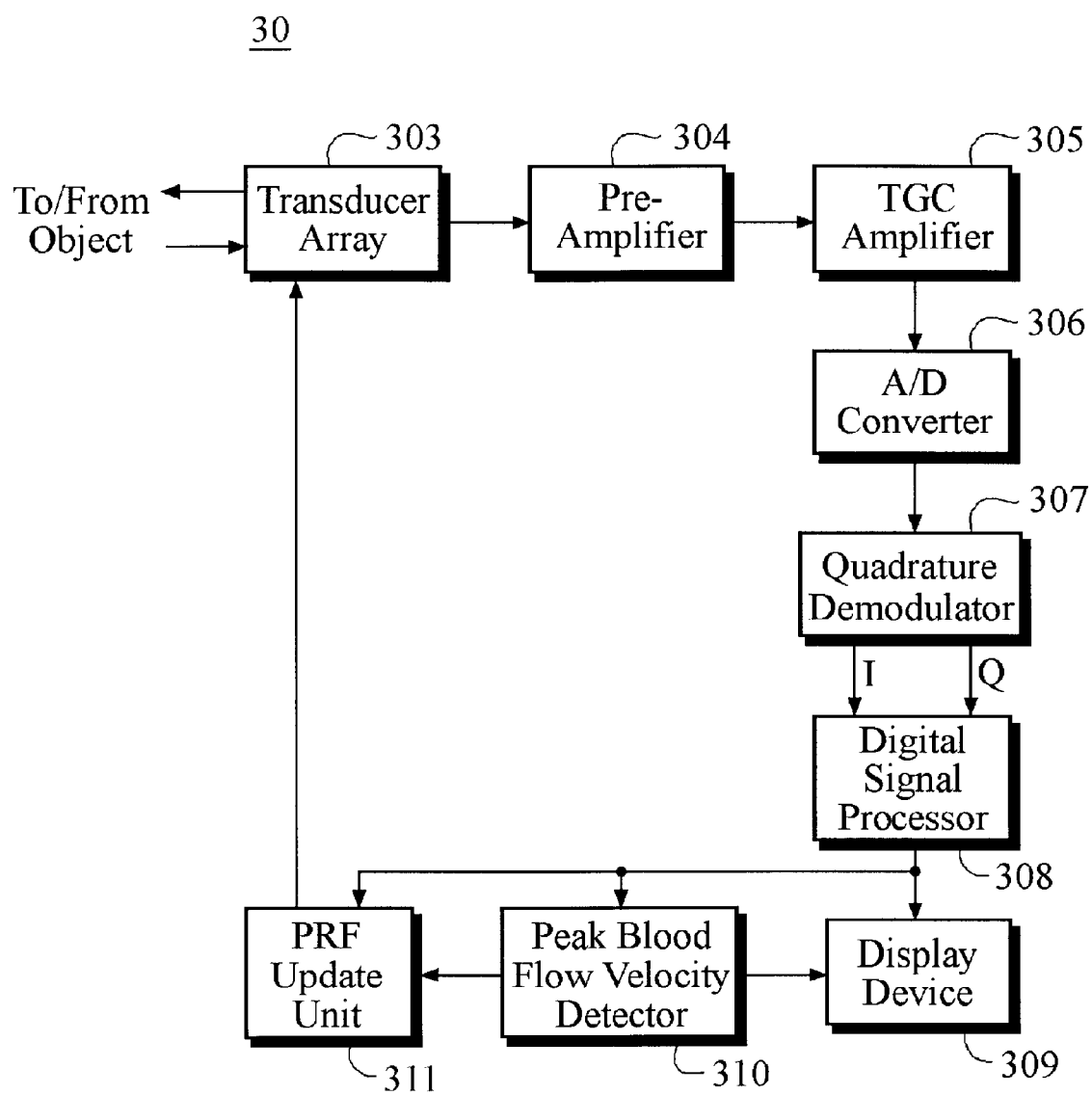
FIG. 3 is a block diagram of an ultrasound diagnostic apparatus for measuring blood flow velocities according to the present invention.

The present invention shown in FIG. 3 is similar to the conventional ultrasound diagnostic system described in the Background of the Invention in that a reflected ultrasound signal, originally transmitted to blood in the human body by a transducer array, is amplified and demodulated. The apparatus 30 comprises a transducer array 303, a pre-amplifier 304, a time-variable gain compensator (TGC) amplifier 305, an analog-to-digital (A/D) converter 306, a quadrature demodulator 307, a digital signal processor 308, a display device 309, and a peak blood flow velocity detector 310.

The received signals undergoes clutter filtering, fast Fourier transforming (FFT) and post-processing to obtain the frequency distribution spectrum. Specifically, the clutter reflected from slowly moving organ and muscle compared to the blood is removed from the demodulated signal by a high-pass filter before the frequency distribution data of 2N frequency components are generated from the filtered signal by using a well known FFT technique.

Figure 4:
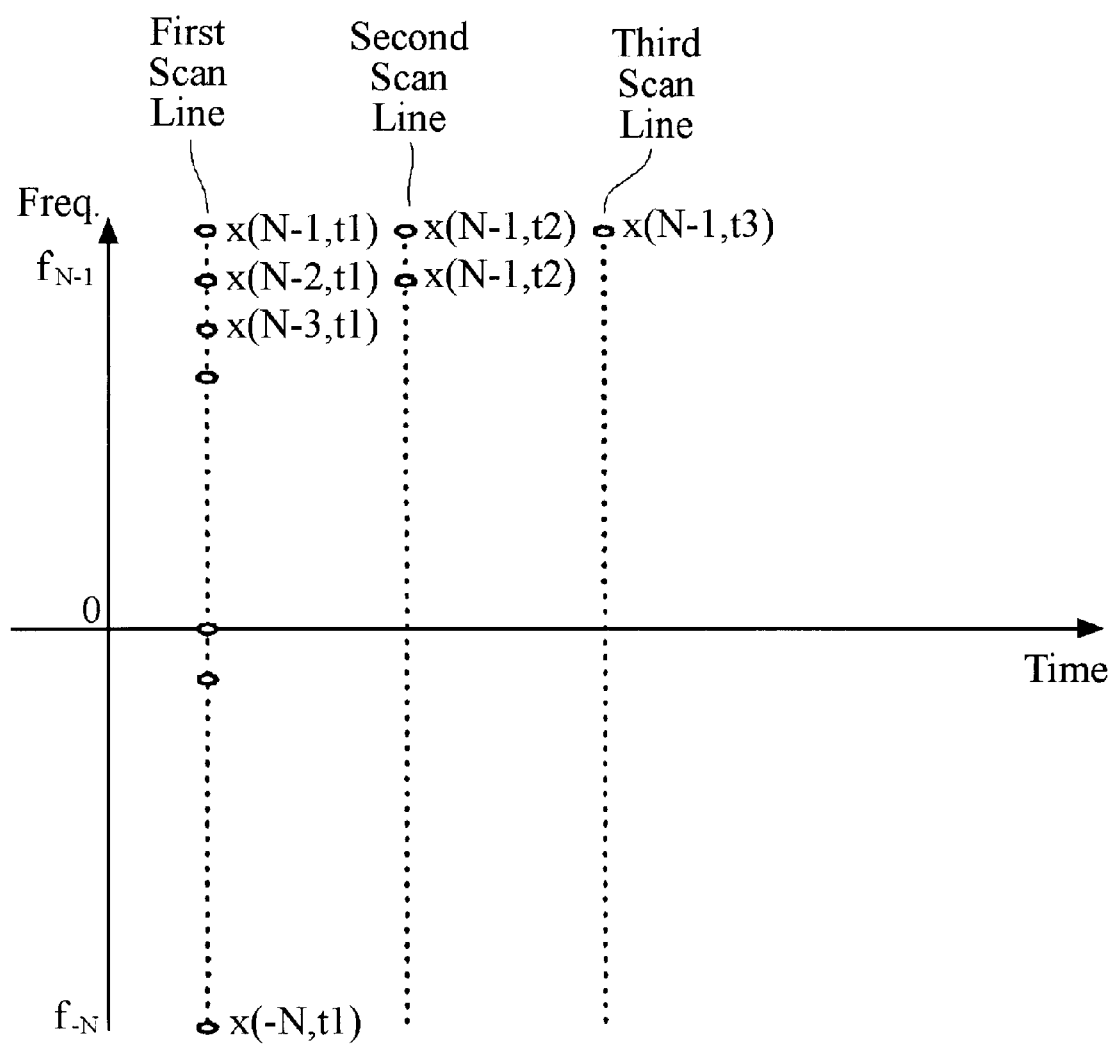
FIG. 4 is a graph displaying the frequency distribution data at a few instants of time.

FIG. 4 is a graph displaying the frequency distribution of a reflected ultrasound signal at each instant of time on a display device 309 of an ultrasound diagnostic system 30 shown in FIG. 3. In FIG. 4, each of scan lines is a graphical representation of 2N frequency distribution data of the reflected ultrasound signal at an instant of time. For example, an M-th scan line represents a set of 2N frequency components obtained at a particular time $t_M$. The power level of a frequency $f_i$ on the M-th scan line is here denoted by $x(i, t_m)$ and usually indicated on the display screen in gray scale. The higher the power level is the brighter the point is. By definition, $x(i, t_M)$ also represents a velocity of the blood flow at time $t_M$.

As briefly mentioned in the Background of the Invention above, if a PRF (pulse repetition frequency) is not sufficiently higher than the blood flow velocity, aliasing occurs. The aliasing causes a mirror image of high negative frequencies to appear in the high frequency domain, which is a phenomenon well known in a digital signal processing technology. In this situation, an accurate estimation of a noise level is not possible because reflected signal components would be influence the noise threshold. As a result, a method for detecting whether or not an aliasing occurs in a sample data about one scan line and a method for updating the PRF in order to prevent the aliasing should be needed to the prior art. For this purpose, as shown in FIG. 3, the ultrasound diagnostic apparatus 30 further comprises a PRF update unit 311 that automatically updates the PRF to avert the occurrence of aliasing.

Figure 5:
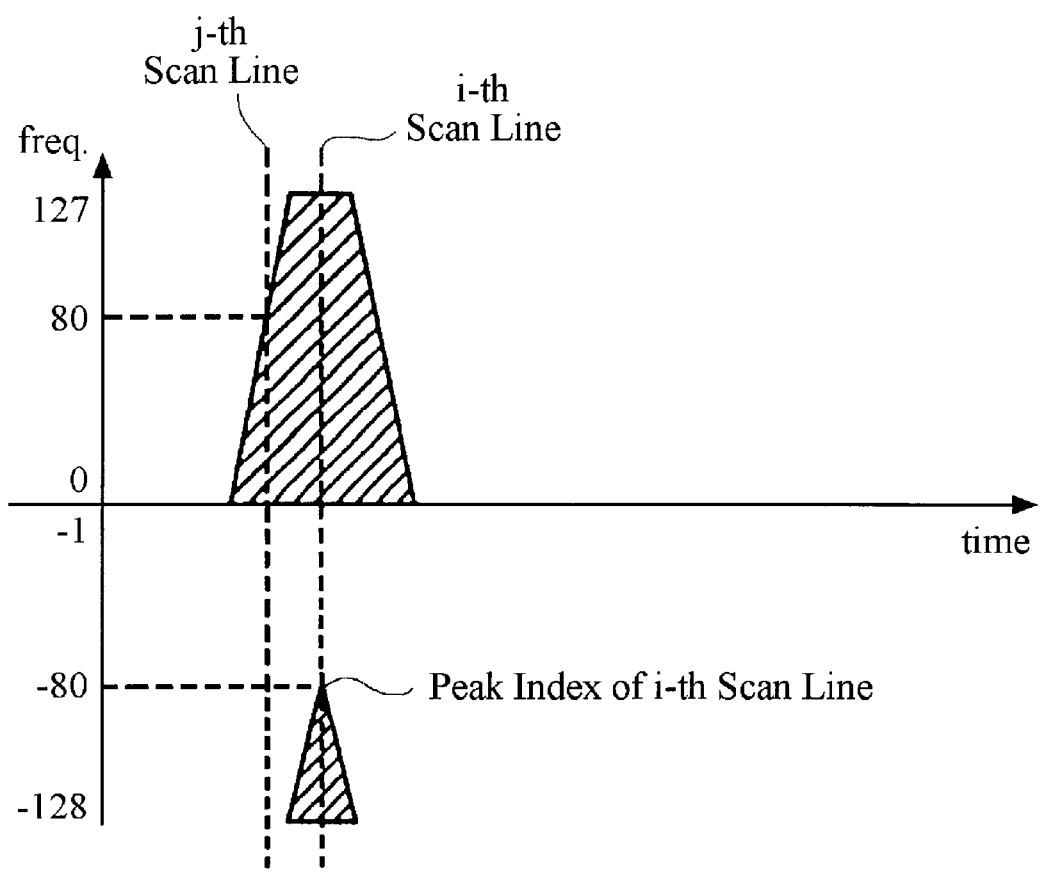
FIG. 5 is a graph displaying the frequency distribution in case of aliasing occurrence.

The PRF is automatically updated by the PRF update unit 311 such that the aliasing does not occur. This aspect of the present invention will be described referring to FIG. 5 showing a graph displaying the frequency distribution in case of occurrence of aliasing, where the X and Y axes represent time and frequency, respectively. For the sake of convenience, the frequency here is identified by the index in the frequency distribution, i.e., one of 2N numbers.

Shaded areas in FIG. 5 correspond to their frequency components whose power levels are above the noise threshold. Bearing in mind that the peak index in a given scan line corresponds to the fastest components of blood flowing in a same direction, the sign of the peak index would be inconsistent with the direction of the blood flow when aliasing occurs because the highest frequency portion folds over to the other frequency domain. Thus, by comparing the direction of blood flow with the sign of the peak index, one can tell whether aliasing has occurred. In other words, the sign of a frequency domain which was determined to include reflected signal components (the sign indicating the direction of blood flow) is compared with the sign of the peak index to determine the occurrence of aliasing. When aliasing is detected to have occurred, the PRF is updated depending on the magnitude of the peak index in such a way that the alias does not occur.

To elaborate on this inventive feature, FIG. 5 is further explained. The peak index for an j-th scan line is 80. For the j-th scan line, it is seen that the alias did not occur the peak frequency as well as the rest of frequency components above the threshold are all positive. Now let's examine the i-th scan line. Despite that the sum of the power levels of the positive frequency components is greater than that of the negative components, the peak index is negative, indicating that aliasing occurred. In other words, the frequency components shown in the negative domain are not because of blood cells flowing away from the transducer but because of folding over the positive higher frequency components. In this case, the detected blood flow velocities are considered to have reliabilities. The largest absolute frequency index, i.e., the half of the frequency distribution 2N, is shown to be 128 in FIG. 5 When the blood flow is slow, aliasing does not occur, for example, at the j-th instant. It follows that the PRF for the j-th scan line does not need to be adjusted. But at the i-th scan line, the PRF should be increased to increase the largest index. In other words, the new largest frequency index $N_{new}$ to avoid the alias is determined as follows:

$$N_{new} = N_{old} + (N_{old} - |\text{peak\_index}|) = 2N_{old} - |\text{peak\_index}| \quad \text{Eq.(1)}$$

where $N_{old}$ is a current largest frequency index. For example, in FIG. 5, because $N_{old}$ is 128 corresponding to the half of the frequency distribution 2N, and the peak index of the i-th scan line is −80, $N_{new}$ is computed to be 176 according to the above equation. That is, the largest frequency index should be increased to 176 in order to avoid aliasing. Because the largest frequency index is proportional to the PRF, the PRF for avoiding the alias gets increased as determined by the following equation:

$$PRF_{new} = PRF_{old} \frac{N_{new}}{N_{old}} \quad \text{Eq. (2)}$$

Where, $PRF_{new}$ is an updated PRF for preventing the aliasing, and $PRF_{old}$ is an old PRF before updating.

If the Eq. (1) is applied to the Eq. (2), the current PRE value $PRF_{old}$ can be updated to a new PRF $PRF_{new}$ for avoiding aliasing according to the following equation (3):

$$PRF_{new} = PRF_{old}\left(2 - \frac{|\text{peak\_index}|}{N_{old}}\right) \quad \text{Eq. (3)}$$

Where, |peak_index| is the absolute value of a peak frequency index, and $N_{old}$ is the largest frequency index of a frequency distribution data generated from the $PRF_{old}$.

Figure 6:
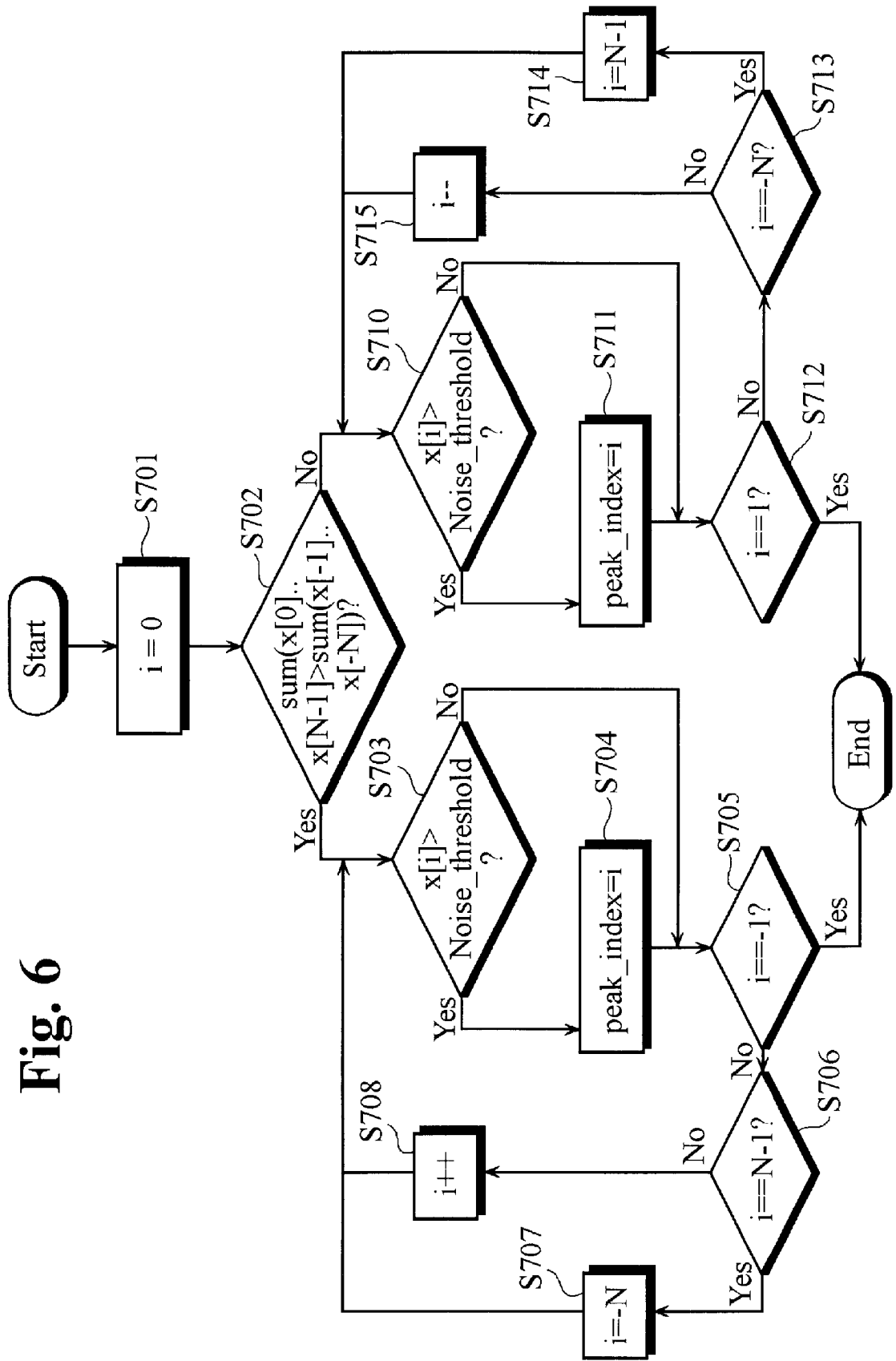
FIG. 6 shows a flow chart for explaining a method of computing the peak index of a scan line in accordance with the present invention.

FIG. 6 shows a flow chart for explaining a method of computing the peak index of a scan line in accordance with the present invention. Here, i represents the frequency index and x[i] represents the power level of the i-th frequency component. The largest positive frequency index of the scan line is N−1 and the largest negative frequency index of the scan line is −N.

First, i is initialized to 0 (S701). Next whether a reflected signal exists within the positive frequency range or negative range is determined (S702). If in the positive frequency range (S702), it is inspected whether x[i] is above the noise threshold (S703) and, if so, the peak index is updated to i (S704). Otherwise it is determined whether i is equal to −1 (S705) and, if so, it signals that the peak index has been found. If i is not equal to −1 (S705), then it is further checked whether i =N−1 or not (S706). If i=N−1 (S706), i is set to −N (S707). If not, i is increased by one (S708). The power level of the new index value is computed in the same way.

If the reflected signal existed in the negative frequency range, the same peak index is determined in the same manner except that the index i is decreased from zero to −N and then from N−1 to 1. That is, if the reflected signal existed in the negative frequency range (S702), it is inspected whether x[i] is above the noise threshold (S710) and, if so, the peak index is updated to i (S711). Otherwise it is determined whether i is equal to 1 (S712) and, if so, it signals that the peak index has been found. If i is not equal to 1 (S712), then it is further checked whether i=−N or not (S713). If i=−N (S713), i is set to N−1 (S714). If not, i is decreased by one (S715).

To further understand the above concept of FIG. 6, let's apply the concept of FIG. 6 to FIG. 5.

For the j-th scan line of FIG. 5, because x[i] is above the noise threshold for i from 0 to 80, the peak index is updated. But for i from 81 to N−1 and −N to −1, x[i] is not above the noise threshold, the peak index is not updated. Accordingly, after the power levels of all the indices are considered, the peak index is determined to be 80. On the other hand, for the i-th scan line shown in FIG. 5, the peak index is updated while i=0 to i=N−1 and i=−N to i=−80. But for i=−79 to −1, the peak index is not updated. Accordingly, after checking power levels for all the indices, the peak index becomes −80.

Figure 7:
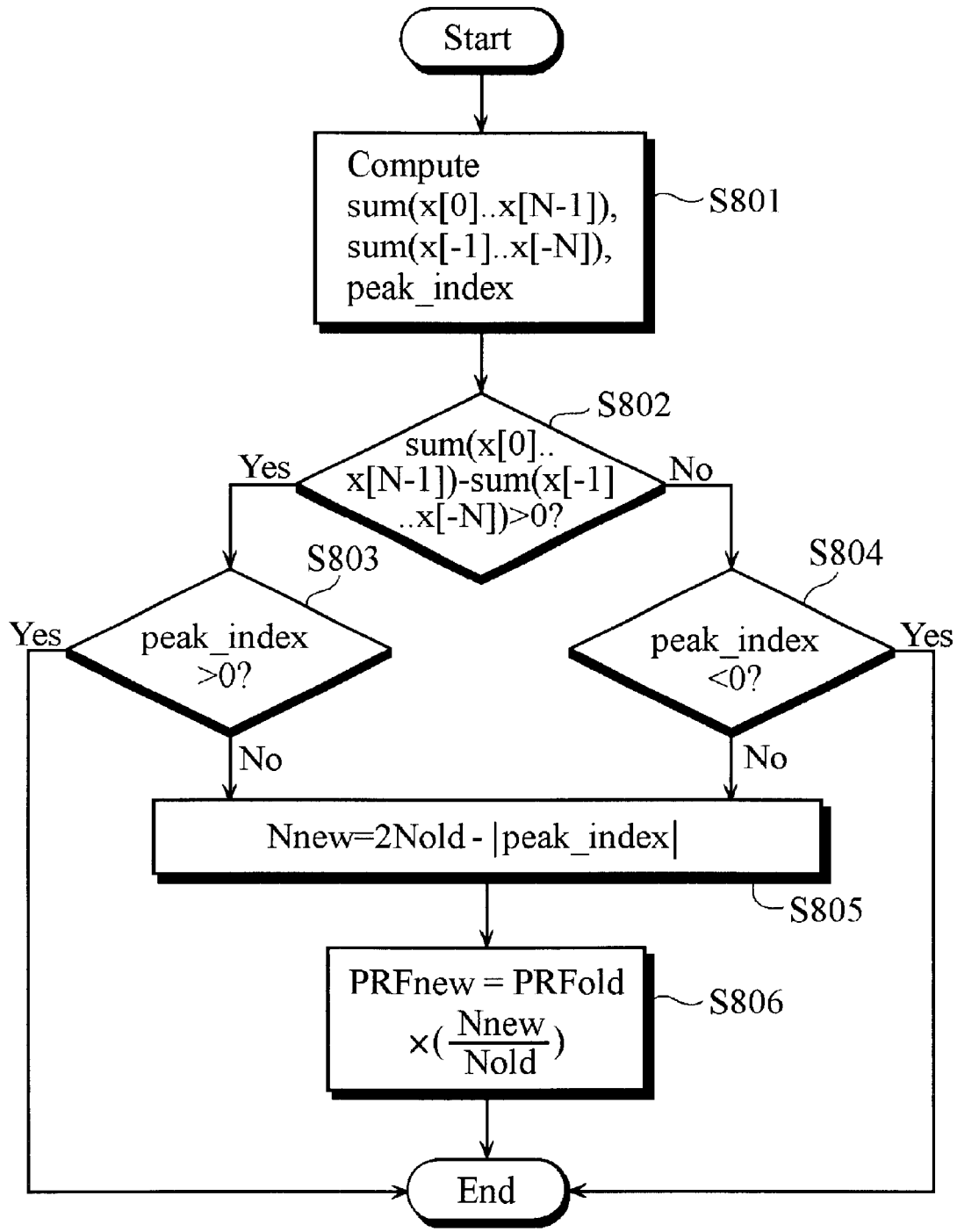
FIG. 7 shows a flow chart for explaining a method of updating the PRF of a scan line in accordance with the present invention.

FIG. 7 offers a flow chart for explaining a method of updating the PRF of a scan line in accordance with the present invention. The peak index is computed (S801) as is shown in FIG. 6. Then it is determined (S802) whether the signal exists in the positive frequency range or the negative frequency range. If the signal exists in the positive frequency range, it is further checked whether the sign of the peak index is positive (S803) and, if so, the PRF is not updated. That is, if a real signal component exists in a positive frequency range and the peak index is positive, it signals that the aliasing does not occur. Accordingly, without updating the PRF, a program is terminated (S807).

If the peak index is negative, this signals that the aliasing occurs. Accordingly, a new upper bound of the frequency index, i.e., $N_{new}$ in Eq. (1), is computed (S805), a new $PRF_{new}$ not causing the aliasing according to Eq. (2) is computed (S806), and then a program is terminated (S807).

Meanwhile if the signal existed in the negative frequency range (S802), it is further checked whether the sign of the peak index is negative (S804) and, if so, the PRF is not updated. If the sign is positive (S802), a new upper bound of the frequency index, i.e., $N_{new}$ in Eq. (1), is computed (S805). Using the new largest frequency index, a new PRF, i. e., $PRF_{new}$ in Eq. (3), is computed.

Although FIG. 7 firstly employs the Eq. (1) in the step (S805) and then employs the Eq. (2) in the step (S806), the $PRF_{new}$ can be computed by using Eq. (2) not the Equations (1,2).

As described above, the inventive ultrasound diagnostic apparatus and method detect whether the aliasing occurs in sample data in measuring a blood flow velocity. If the aliasing occurs, the inventive ultrasound diagnostic apparatus and method determine an optimum PRF by updating a current PRF such that the aliasing does not occur.

While there has been described and illustrated system and method for updating a pulse repetition frequency(PRF) to avoid aliasing, it will be apparent to those skilled in the art that variations and modifications are possible without deviating from the broad principles and teachings of the present invention which should be limited solely by the spirit and scope of the claims appended hereto.

What is claimed is:

1. An ultrasound diagnostic apparatus, comprising:

means for generating sample data by transmitting an ultrasound signal into a human body and sampling a reflected signal of the ultrasound signal;

means for generating frequency distribution data by processing the sample data, wherein the frequency distribution data includes a number of frequency components, each of the frequency components having a corresponding power level;

means for determining a blood flow velocity on the basis of the frequency distribution data; and means for detecting whether or not an aliasing occurs in the frequency distribution data, wherein the aliasing detecting means computes a peak index corresponding to the fastest blood flow velocity component among frequency components comprising the frequency distribution data, selects a frequency range having the largest sum of power levels of the frequency components between a positive frequency range and a negative frequency range of the frequency distribution data, compares the selected frequency range with the peak index, and determines whether an aliasing occurs or not.

2. The ultrasound diagnostic apparatus of claim 1, further comprising:

means for updating a pulse repetition frequency(PRF) of the sample data in case of sensing the aliasing.

3. The ultrasound diagnostic apparatus of claim 2, wherein the updating means updates the pulse repetition frequency (PRF) according to the following equation:

$$PRF_{new} = PRF_{old}\left(2 - \frac{|peak\_index|}{N_{old}}\right)$$

where, $PRF_{new}$ is an updated PRF for preventing the aliasing, $PRF_{old}$ is an old PRF before updating, peak_index is the peak frequency index corresponding to the fastest blood flow velocity component, and $N_{old}$ is the largest frequency index of a frequency distribution data generated from the $PRF_{old}$.

4. The ultrasound diagnostic apparatus of claim 1, wherein the blood flow velocity detecting means determines that a reliability of a detected blood flow velocity is very low in case that the aliasing detecting means detects the aliasing.

5. An ultrasound diagnostic method for measuring a blood flow velocity, comprising the steps of:

(a) generating sample data by transmitting an ultrasound signal into a human body and sampling a reflected signal of the ultrasound signal;

(b) generating frequency distribution data by processing the sample data, wherein the frequency distribution data includes a number of frequency components, each of the frequency components having a corresponding power level;

(c) determining a blood flow velocity on the basis of the frequency distribution data; and (d) determining whether or not an aliasing occurs in the frequency distribution data, wherein the step for determining the aliasing computes a peak index corresponding to the fastest blood flow velocity component among the frequency components comprising the frequency distribution data, selects a frequency range having the largest sum of power levels of the frequency components between a positive frequency range and a negative frequency range, compares the selected frequency range with the peak index, and determines whether an aliasing occurs or not.

6. The ultrasound diagnostic method of claim 5, further comprising the step (e) for updating a pulse repetition frequency(PRF) of the sample data in case of sensing the aliasing.

7. The ultrasound diagnostic method of claim 6, wherein the step (e) updates the pulse repetition frequency(PRF) according to a following equation:

$$PRF_{new} = PRF_{old}\left(2 - \frac{|peak\_index|}{N_{old}}\right)$$

where, $PRF_{new}$ is an updated PRF for preventing the aliasing, $PRF_{old}$ is an old PRF before updating, peak_index is the peak frequency index corresponding to the fastest blood flow velocity component, and $N_{old}$ is the largest frequency index of a frequency distribution data generated from the $PRF_{old}$.

8. The ultrasound diagnostic method of claim 5, wherein the step (c) for detecting the blood flow velocity determines that a reliability of a detected blood flow velocity is very low in case that the step (d) detects the aliasing.

* * * * *